(12) United States Patent
Wooley (10) Patent No.: US 9,913,467 B2
(45) Date of Patent: Mar. 13, 2018

(54) ANTI-INFECTIVE PROTECTOR

(75) Inventor: Debbie Wooley, Birmingham, AL (US)

(73) Assignee: Ansell Healthcare Products LLC, Iselin, NJ (US)

( * ) Notice: Subject to any disclaimer, the term of this patent is extended or adjusted under 35 U.S.C. 154(b) by 1042 days.

(21) Appl. No.: 12/503,643

(22) Filed: Jul. 15, 2009

(65) Prior Publication Data

US 2010/0028397 A1 Feb. 4, 2010

Related U.S. Application Data

(60) Provisional application No. 61/080,818, filed on Jul. 15, 2008.

(51) Int. Cl.
*A61K 45/06* (2006.01)
*A61K 47/48* (2006.01)
*A61L 29/08* (2006.01)
*A01N 25/34* (2006.01)

(52) U.S. Cl.
CPC .................................. *A01N 25/34* (2013.01)

(58) Field of Classification Search
None
See application file for complete search history.

(56) References Cited

U.S. PATENT DOCUMENTS

| | | | |
|---|---|---|---|
| 3,464,413 A * | 9/1969 | Goldfarb et al. | 604/306 |
| 3,645,835 A * | 2/1972 | Hodgson | 428/195.1 |
| 4,699,838 A | 10/1987 | Gilbert | |
| 4,935,232 A | 6/1990 | McIntosh | |
| 5,069,907 A * | 12/1991 | Mixon et al. | 424/445 |
| 5,300,358 A | 4/1994 | Evers | |
| 5,536,742 A * | 7/1996 | Mason | 514/398 |
| 5,924,584 A | 7/1999 | Hellstrom et al. | |
| 6,395,955 B1 | 5/2002 | Roe et al. | |
| 6,485,667 B1 | 11/2002 | Tan | |
| 7,347,498 B2 | 3/2008 | Clifford | |
| 7,939,149 B2 | 5/2011 | Haskin et al. | |
| 8,025,120 B2 | 9/2011 | Eddy | |
| 2002/0000289 A1 | 1/2002 | Nickell et al. | |
| 2002/0052570 A1* | 5/2002 | Naimer | 602/53 |
| 2003/0082966 A1 | 5/2003 | Menday et al. | |
| 2003/0125680 A1* | 7/2003 | Ding | 604/304 |
| 2006/0006678 A1 | 1/2006 | Herron, Jr. | |
| 2006/0010652 A1 | 1/2006 | Kellaher et al. | |
| 2006/0173430 A1 | 8/2006 | Lee et al. | |
| 2006/0260622 A1 | 11/2006 | Wooley et al. | |
| 2007/0218096 A1 | 9/2007 | Wooley | |
| 2010/0197817 A1 | 8/2010 | Bui et al. | |

FOREIGN PATENT DOCUMENTS

| | | |
|---|---|---|
| JP | 08-337907 | 12/1996 |
| WO | WO 2008/040965 A2 | 4/2008 |

OTHER PUBLICATIONS

Mauriello et al. ("Mauriello", Lett. Appl. Microbio, 2005, 41, 464-469).*

* cited by examiner

*Primary Examiner* — Misook Yu
*Assistant Examiner* — Kauser M Akhoon
(74) *Attorney, Agent, or Firm* — Moser Taboada (57) ABSTRACT

The present disclosure provides an anti-infective protector containing at least one anti-infective agent. The anti-infective protector provides for a range of benefits not appreciated in the prior art.

7 Claims, 3 Drawing Sheets

ANTI-INFECTIVE PROTECTOR

FIELD OF THE DISCLOSURE

The present disclosure relates generally to anti-infective protectors for use in a healthcare setting. Specifically, the present disclosure relates to anti-infective protectors for use in a healthcare setting containing at least one anti-infective agent. Methods of using the anti-infective protectors are also provided.

BACKGROUND

In recent years, the concern regarding exposure to infective agents has increased. In particular, there is increasing concern over nosocomial infections (commonly referred to as hospital acquired infections). A variety of organisms may be responsible for nosocomial infections, such as, but not limited to, bacteria, viruses, fungi and other parasitic species. Exemplary bacterial species responsible for nosocomial *Salmonella, Escherichia coli* O157:H7, *enterococci*, including vancomycin-resistant *enterococci* (VRE), and *Staphylococcus aureus*, including methicillin resistant *S. aureus* (MRSA). In the United States, it has been estimated that as many as one hospital patient in ten acquires a nosocomial infection, or 2 million patients a year. Estimates of the annual cost range from $4.5 billion to $11 billion. Nosocomial infections contributed to 88,000 deaths in the U.S. in 1995. One third of nosocomial infections are considered preventable. Common infections are urinary tract infections, wound infections, pneumonia, or blood stream infections. Nosocomial infections are important causes of morbidity and mortality, and represent a significant economic burden to third party payers and society. It is important that health care providers take the necessary and appropriate means to prevent these infections.

Of particular concern are cases where the nosocomial infection involves agents that are resistant to currently used medical therapies. For example, in the case of bacterial infections, MRSA is of particular concern. MRSA is a strain of *S. aureus* resistant to the β-lactam and cephalosporin antibiotics. Resistance is conferred through a mutated receptor on the bacterial cell surface which prevents the antibiotics' transport inside the cell. MRSA infections are on the rise in the U.S. In 1999, there were approximately 127,000 cases of MRSA reported in the U.S. In 2005, the CDC reported that there were over 278,000 cases of MRSA in the U.S. Deaths from MRSA are also on the rise. In 1999, there were 11,000 deaths reported from MRSA compared to 17,000 deaths in 2005. MRSA imposes a serious economic toll as studies have shown that patients infected with MRSA stay approximately three times longer in the hospital and incur three times the hospital expenses than patients without MRSA infection. Although MRSA and other such infections are difficult to treat once a patient has acquired such an infection, such bacteria may be eliminated from the healthcare setting through the use of agents that may not be well tolerated by the patient. Therefore, eliminating such organisms from the healthcare setting is of importance.

One source of nosocomial infection is the transmission of infective agents from a patient to equipment present in a healthcare setting, resulting in colonization of the equipment. Such transmission can result from exposure of equipment to a patient's blood and/or other bodily fluids or exposure of equipment to a patients exterior, such as, but not limited to, skin, hair and clothing. Furthermore, the equipment may be exposed to blood/bodily fluids/exterior of healthcare workers or friends and family that may be visiting the patient or others in the healthcare setting. Finally, equipment may be exposed to infective agents through ambient environmental conditions in the healthcare setting. Other types of exposure are also be contemplated.

For example, in a surgical setting, bodily fluids from a patient, such as blood, drainage from a site of infection etc., often contact equipment used in the surgical setting. Such equipment includes, but is not limited to, patient tables, patient table mattress and surgical instruments/supplies, including without limitation cameras, x-ray machines, microscopes and other diagnostic equipment. Such exposure can lead to the colonization of equipment by infective agents. Such colonization can increase the incidence of nosocomial infection in patients present in the healthcare setting. Furthermore, colonization of equipment can also lead to infection of others present in the healthcare setting, such as but not limited to, friends and family and healthcare workers, allowing these infections to be spread beyond the boundaries of the healthcare setting.

The foregoing is equally applicable to other environments in a healthcare setting, such as a private home, post-operative recovery area, emergency room, patient room, diagnostic area or doctor's office.

Despite the abundance of products available for the control of transmission of infective agents to equipment in a healthcare setting and control of the resulting colonization should such transmission occur, transmission and colonization, along with the resulting impact on health and healthcare economics, continue to increase. Therefore, the prior art is in need of improved devices and methods to reduce or prevent the transmission of infective agents to equipment present in a healthcare setting and to reduce or eliminate colonization of such equipment if such transmission does occur.

The present disclosure provides addresses the shortcomings of the prior art by providing a novel anti-infective protector for use in a healthcare setting.

BRIEF DESCRIPTION OF DRAWINGS

It should be noted that identical features in different drawings are shown with the same reference numeral.

DETAILED DESCRIPTION

With hospital acquired infections (HAIs) at an all time high and rapidly proliferating, it is clear, that despite all the current infection control measures to prevent HAIs, the battle is being lost. It is known and accepted that contamination and cross contamination play a role in the spread of HAIs. Furthermore, it can be argued that there is a false sense of security among both the public and the medical community when it comes to the level of contamination pertaining to the medical equipment routinely used, on a daily basis, in the healthcare setting. That false sense of security is primarily based on the belief that if the surface area of medical equipment is wiped down with a disinfectant (which is standard procedure) the equipment is rendered free from contamination. To the contrary, the fundamental design of most heath care equipment makes it virtually impossible to completely decontaminate the surface area of this equipment due to the crevices, adapters, assorted buttons, switches and alarms that are an integral part of the surface design of the equipment. Therefore the standard and universally accepted practice of wiping down medical equipment and other surfaces with a disinfectant is not effectively decontaminating the equipment.

Infective agents, such as but not limited to bacteria, can thrive and multiply profusely in small cracks and crevices for long periods of time. In fact, many infective agents prefer just such areas to multiply due to the dark, moist, and warm nature of the areas. The foregoing may lead to serious contamination and cross contamination.

For example, in the case of an IV infusion pump, the outer surface has many buttons and switches and alarms that are constantly being activated, deactivated and touched by the patient, the nurses, the lab technicians, the respiratory therapist, the housekeepers, the dietary personnel and even the physicians. In this example, suppose the IV Infusion pump is at the bedside of a terminally ill patient that is infected with MRSA. Standard procedure is that the pump, along with most equipment, would not be covered in any form or fashion. Therefore, no covers currently exist. Typically, once the patient is discharged or expires the pump is then taken through the healthcare setting to a processing/storage room to be wiped down and stored until its next use. The following day the infusion pump is brought to the bedside of a 14 year old girl undergoing chemotherapy for leukemia. This infusion pump that was less than 24 hrs ago administering intravenous fluids to a patient with MRSA is now delivering chemotherapy to an immune-compromised child with the likelihood that the surface of the pump is growing MRSA bacteria. So, as the nurses and family members touch this pump and then touch the patient or the other surfaces in the patient's room they are now cross contaminating the environment and the patient with whatever is growing on that pump, including MRSA bacteria. In addition, they are introducing more new infective agents to the already contaminated pump.

The present disclosure provides an anti-infective cover to address this situation. The use of the anti-infective protector (i) prevents transmission of infective agents to the pump (such as from the prior patient, healthcare workers, the present patient, others in the healthcare setting and the environment), (ii) prevents the colonization of the pump with infective agents and (iii) prevents transmission of infective agents from the pump to the current patient, healthcare workers, the environment and others in the healthcare setting. Furthermore, since the anti-infective protector comprises an anti-infective agent, the growth of any infective agents introduced during use is reduced or eliminated. At the end of use the cover is removed and discarded. As a result, the contamination of the healthcare environment during transportation of the pump from the bed side to the decontamination area is reduced or avoided, the healthcare worker responsible for cleaning the pump is not exposed and the pump is safer for the next patient.

The above concerns also extend to the operating room setting. There are many pieces of equipment necessary for a surgical procedure that are simply too large or too sensitive to withstand the sterilization process. However, the equipment must be brought into the sterile field in order to be used. In this case, standard procedure is to drape the equipment with a sterile drape. However, placing a sterile drape over a particular piece of equipment does not guarantee that the sterility continues throughout the procedure. The sterile drape may be contaminated either in the application or once the piece of equipment is put into use by the sterile or non-sterile members of the surgical team. It is important to note that everything above the shoulders and below the waist on healthcare workers (even those scrubbed and a part of the sterile field) is considered non-sterile. Therefore, such sterile drapes can often be contaminated during application and use. The large size of some equipment makes this even more likely. Often the sterility of the drape is compromised without anyone realizing it. For example, the surgeon may accidentally and unknowingly contaminate the sterile drape simply by using it in such a way that it comes in contact with an area of his body that is considered non-sterile. A surgical microscope is a good example. As the surgeon leans in to look through the oculars, the face, facemask, nose and eyes may contaminate that drape by touching it. During the normal course of using a surgical microscope it is common for a surgeon to reach up in the middle of a procedure with a sterile gloved hand and manipulate the now contaminated drape over the oculars that are assumed to still be sterile. These gloved hands are now contaminated and may be put into contact with the patient's body. As a surgical procedure can last anywhere from 15 minutes to 15 hours, infective agents can quickly multiply and migrate.

The foregoing is also applicable to equipment that is not brought into the sterile field but is in close proximity. A variety of equipment is used in a procedure that is not brought in the sterile field is not protected from contamination in any fashion. However, this equipment can become grossly contaminated by infective agents, such as by airborne droplets, blood, body fluids, bone chips, bloody sponges, etc. This equipment will most likely be used on the next patient brought into the operating room or it may follow the patient to the recovery area and then transported to a final destination. In any event, the equipment remains contaminated and is a threat to the patient, other patients, healthcare workers and others in the healthcare setting.

The present disclosure provides an anti-infective protector to address this situation. The use of the anti-infective protector (i) prevents transmission of infective agents from equipment and the like used in and outside the sterile field to the patient; (ii) maintains the sterility of the sterile field by reducing or eliminating infective agents that may be transmitted from the physician or the environment into the sterile field and (iii) prevents the colonization of the equipment with infective agents (both inside and outside the sterile field. Furthermore, since the anti-infective protector comprises an anti-infective agent, the growth of any infective agents introduced during use is reduced or eliminated. At the end of use the cover is removed and discarded. As a result, the contamination of the healthcare environment and sterile field is reduced and the environment is safer for next patient.

Once a procedure is completed a process known as room turnover begins. During this process the goal is to decontaminate horizontal surfaces, cleanup any visibly soiled walls or equipment, remove all trash, linens, infectious liquid waste, collect all the contaminated instruments and remove the foregoing from the room. The equipment used is either pushed to the walls for use on the next procedure or taken to a storage area. This is all done in a hurried fashion as the next patient is usually in the hallway waiting to be brought into the operating room. Once the room is cleaned, new equipment and other materials are brought in and the room prepared for the next surgery. However, as discussed above, many pieces of equipment may be contaminated even though not in direct contact with the patient. Furthermore, cursory wiping down is not effective in eliminating infective agents from cracks and crevices present in most equipment.

The present disclosure provides an anti-infective protector to address this situation. The use of the anti-infective protector (i) prevents transmission of infective agents to various pieces of equipment thereby preventing or reducing colonization; (ii) aids in more efficiently carrying out the room turnover procedure and (iii) creates a safer environment for the patient, healthcare workers and others present in the healthcare setting.

As the above exemplifies, new devices and methods are needed to control the transmission of infective agents in a healthcare setting. The present disclosure provides such a solution.

Definitions

"About" and "approximately" as used herein shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated "Anti-infective agent" as used herein means any drug, chemical, or other substance that kills and/or slows the growth of an infective agent; the term includes antibacterial agents, antiviral agents, antifungal agents, and antiparisitic drugs.

"Colonization" as used herein means the establishment of an infective agent on a piece of equipment or a subject.

"Controlled release" as used herein means the release of the anti-infective agent from the infection protector in a manner that is modified from an immediate release composition. The modified release may be a sustained release, a slow release, a prolonged release, a triggered release or a combination of the foregoing. In a particular embodiment, the controlled release is a triggered release.

"Equipment" as used herein is meant to be interpreted broadly to include any equipment used in a healthcare setting (such as, but not limited to, patient tables, patient table mattress and surgical instruments/supplies, including without limitation, cameras, x-ray machines, microscopes and other diagnostic equipment) and surfaces (such as, but not limited to, tables, chairs, counters, cabinets, etc.) that may be present in the healthcare setting whether or not such surfaces are part of any piece of equipment; the term also is meant to include interior and exterior portions (such as in the case of a surgical mattress) where relevant.

"Healthcare setting" as used herein means any setting in which a subject or patient receives medical care; examples include but are not limited to a hospital, a doctor's office, a waiting room, a patient room, a home, an operating room, or a diagnostic room. Also included are those settings in which animals receive medical care.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

"Infective agent" as used herein means any known agent that is capable of negatively impacting the health of a subject such as, but not limited to, any agent capable of causing an infection, such as but not limited to a nosocomial infection; such organisms include, but are not limited to, bacteria (both gram positive and gram negative), viruses, parasites and fungi. In a specific embodiment, the infective agent is *Salmonella, Escherichia coli* O157:H7, vancomycin-resistant *Enterococci* (VRE) or *Staphylococcus aureus*, including methicillin resistant *S. aureus* (MRSA).

"Individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

"Nosocomial infection" as used herein means any infections which are a result of treatment in or exposure to a healthcare setting, but are secondary to the patient's original condition; in a specific embodiment, the nosocomial infection is a urinary tract infections, wound infections, pneumonia, or blood stream infections.

"Prevent", "preventing", "prevention", "reduce", "reducing", "reduction" "suppression", "suppress", and "suppressing" as used herein refer to a course of action that reduces the occurrence of a particular event, whether in whole or in part.

The term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial.

SUMMARY

The present disclosure provides an anti-infective protector containing at least one anti-infective agent. As a result, the anti-infective protector provides for a range of benefits not appreciated in the prior art.

The current disclosure provides an anti-infective protector useful for preventing or eliminating the transmission of infective agents to equipment, patients and others, such as in a healthcare setting. Additionally, the current disclosure provides an anti-infective protector useful for reducing or eliminating the colonization of equipment, patients and others in a healthcare setting. Further, the current disclosure provides an anti-infective protector useful for reducing or eliminating the incidence and/or spread of nosocomial and other infections.

Still further, the current disclosure provides an anti-infective protector useful for maintaining a sterile field by providing a barrier for non-sterile elements, such as medical equipment, that may be required for use in the sterile field, thereby preventing the sterile field from being contaminated by such elements. In yet another embodiment, the present disclosure provides for an anti-infective protector useful for maintaining a sterile field by inhibiting or eliminating the growth and reproduction of infective agents that may come into contact with the anti-infective protector covering such non-sterile elements and preventing the colonization of such non-sterile elements by infective agents if the barrier is breached. In still a further embodiment, the present disclosure provides an anti-infective protector useful in providing a barrier between contaminated equipment and the healthcare setting, thereby protecting the healthcare setting against colonization from infective agents that may be present on the contaminated equipment.

Finally, in another embodiment, the present disclosure provides an anti-infective protector useful for inhibiting or eliminating the growth or reproduction of infective agents to which the anti-infective protector may have been exposed.

The current disclosure also provides an anti-infective protector useful in a method of preventing or eliminating the transmission of infective agents to equipment, patients and others, such as in a healthcare setting. Additionally, the current disclosure also provides an anti-infective protector useful in a method of reducing or eliminating the colonization of equipment, patients and others in a healthcare setting. Further, the current disclosure also provides an anti-infective protector useful in a method for reducing or eliminating the incidence and/or spread of nosocomial and other infections.

Still further, the current disclosure provides an anti-infective protector useful in a method of maintaining a sterile field by providing a barrier for non-sterile elements, such as medical equipment, that may be required for use in the sterile field, thereby preventing the sterile field from being contaminated by such elements. In yet another embodiment, the present disclosure provides for an anti-infective protector useful in a method of maintaining a sterile field by inhibiting or eliminating the growth and reproduction of infective agents that may come into contact with the anti-infective protector covering such non-sterile elements and preventing the colonization of such non-sterile elements by infective agents if the barrier is breached. In still a further embodiment, the present disclosure provides an anti-infective protector useful in a method of providing a barrier between contaminated equipment and the healthcare setting, thereby protecting the healthcare setting against colonization from infective agents that may be present on the contaminated equipment.

Finally, in another embodiment, the present disclosure provides an anti-infective protector useful in a method of inhibiting or eliminating the growth or reproduction of infective agents to which the anti-infective protector may have been exposed.

Furthermore, the current disclosure provides for methods of preventing or reducing or eliminating the transmission of infective agents from a patient to equipment, from others (such as healthcare workers and friends and family) to equipment, from the ambient environment to equipment and from equipment to the environment, a patient or others (such as healthcare workers and friends and family). Colonization of equipment is also reduced or eliminated if transmission of an infective agent to such equipment has occurred previously, with the aforementioned benefits. In one embodiment, the equipment, patient and others are present in a healthcare setting.

As a result, contamination and cross contamination in a healthcare setting is reduced or eliminated. For example, transmission of infective agents to equipment is reduced or eliminated and/or colonization of equipment in a healthcare setting is reduced or eliminated, with the result that patient health is increased, the potential for spreading infection from or to the patient, the healthcare setting and healthcare workers and others present in the healthcare setting is reduced or eliminated.

In one embodiment, an objective of the present disclosure is to provide an anti-infective protector that creates a barrier to reduce or eliminate the transmission of infective agents to sterile or non-sterile equipment, thereby reducing or eliminating colonization of the equipment by infective agents.

As a result of the foregoing, the following uses and objectives may be achieved.

One objective of the present disclosure is to provide an anti-infective protector that creates a barrier for reducing or eliminating the transmission of infective agents to sterile or non-sterile equipment, thereby reducing or eliminating colonization of the equipment by infective agents.

Another objective of the present disclosure is to provide an anti-infective protector that creates a barrier as described above but also reduces or eliminates the reproduction and/or spread of infection agents on the surface of the anti-infective protector after the anti-infective protector is exposed to such infective agents. For example, the anti-infective protector may by cytotoxic to the infective agent, thereby destroying the infective agent, or may be cytostatic to the infective agent, thereby slowing or eliminating growth and reproduction of the infective agent.

A further objective of the present disclosure is to provide an anti-infective protector that creates a barrier as described above but also reduces or eliminates colonization of infective agents that may be present on or in the equipment, such as may be due to prior colonization of the equipment by an infective agent. For example, the anti-infective protector may by cytotoxic to the infective agent, thereby destroying the infective agent, or may be cytostatic to the infective agent, thereby slowing or eliminating growth and reproduction of the infective agent.

Still further, an objective of the present disclosure is to provide an anti-infective protector that creates a barrier to protect a sterile field from contamination of non-sterile elements, such as, but not limited to, medical equipment, that may be required for use in the sterile field. In many cases, such elements are large for effective sterilization or cannot withstand sterilization from heat gas or solutions and maintain functionality. In such cases, the anti-infective protector provides a barrier that allows such non-sterile elements to be used in the sterile field and at the same time prevents such non-sterile elements from contaminating the sterile field.

Yet another objective of the present disclosure is to provide an anti-infective protector that creates a barrier to protect a sterile field from contamination of non-sterile elements, such as, but not limited to, medical equipment, that may be required for use in the sterile field while at the same time preventing colonization of the anti-infective protector from anti-infective agents may come into contact with the anti-infective protector covering. Furthermore, the anti-infective protector provides the same benefits to the non-sterile elements at the same time as providing the barrier function prevents colonization of the equipment from infective agents that may come into contact with such elements, such as in the case of a breach to the integrity of the anti-infective protector. The infective agents may be generated from the patient, a non-sterile object coming into contact with the anti-infective protector, by air born particulates landing on the anti-infective protector during a sterile procedure, by air born droplets coming in contact with the sterile surface, or by the eventual migration of infective agents from the non-sterile element it is covering.

Still a further objective of the present disclosure is to provide an anti-infective protector that creates a barrier between elements that are or may be colonized with infective agents, such as medical equipment, and the healthcare setting, which has not been exposed to such infective agents. This objective is useful when transporting elements from one point to another, such as transporting the elements from a surgery area to a decontamination area or transporting such elements from a beside use in a patient room to a decontamination area. Cross-contamination of the healthcare setting will thereby be reduced or eliminated.

Still a further objective of the present disclosure is to provide an anti-infective protector that creates continues to provide its beneficial effects after use. For example, when an anti-infective protector of the present disclosure has been used, the anti-infective protector must then be disposed of. Any infective agents remaining on or in the anti-infective protector will continue to be subject to the anti-infective agents comprising the anti-infective protector and the growth and/or reproduction of the infective agents will be reduced or eliminated. Such an objective also protects those parties that come into contact with the anti-infective protector during the disposal process.

Multi-Layer Anti-Infective Protector

Figure 1:
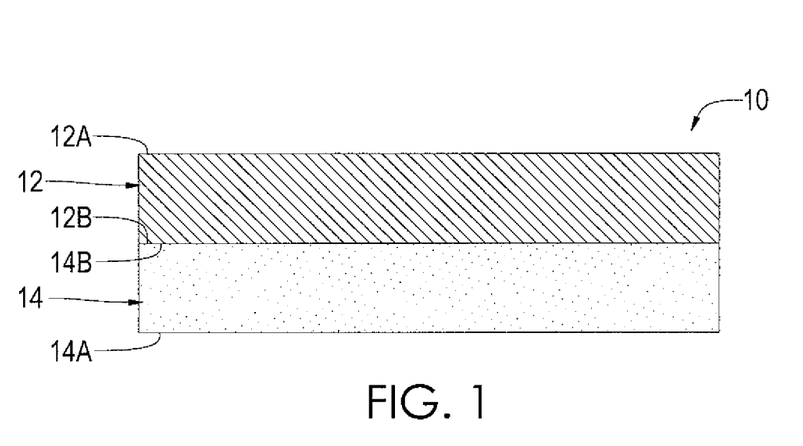
FIG. 1 shows a cross sectional view of one embodiment of an anti-infective protector of the present disclosure.
Figure 2:
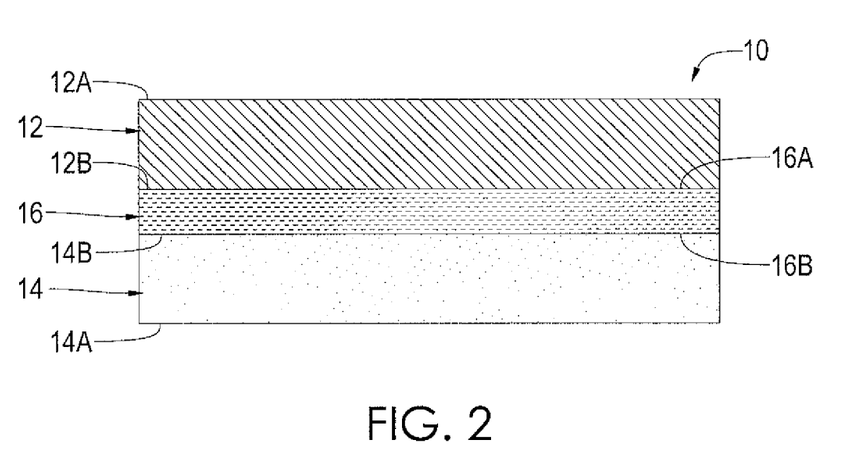
FIG. 2 shows a cross sectional view of an alternate embodiment of an anti-infective protector of the present disclosure

The anti-infective protector of the present disclosure is illustrated in FIGS. 1-2. With reference to FIG. 1, the anti-infective protector 10 comprises an upper portion 12 and a lower portion 14. In one embodiment (shown in FIG. 2), the anti-infective protector 10 further comprises a middle layer 16 positioned between the upper portion 12 and a lower portion 14. The upper 12, lower 14 and middle 16 portions may comprise a single layer of material or multiple layers of materials. In one embodiment, the upper 12, lower 14 and middle 16 portions comprise a single layer of materials.

Regardless of the number of individual layers comprising the upper 12, lower 14 and middle 16 portions, each portion has two surfaces as defined: the upper portion 12 has two surfaces, a first exposed surface 12A and a first interior surface 12B; the lower portion 14 has two surfaces, a second exposed surface 14A and a second interior surface 14B; and the middle portion has two surfaces, a third interior surface 16A and a fourth interior surface 16B.

Upper Portion

The upper portion 12 is a liquid permeable layer that allows at least a portion of any liquid that contacts the upper portion 12 to pass through the upper portion 12. The upper portion 12 may comprise one layer of liquid permeable material or more than one layer of liquid permeable material. In the case where the upper portion 12 comprises more than one layer of liquid permeable material, such layers may be positioned adjacent to and/or bonded to one another. Suitable materials include, but are not limited to, perforated film layers; fabric layers such as woven, non-woven and knitted fabric layers; foam layers and combinations thereof. In one exemplary embodiment, the liquid permeable layer comprises a non-woven fabric, such as a spun-bonded fabric, a spun-laced fabric, a needle-punched fabric, or any combination thereof.

The liquid permeable layer(s) may be formed from a variety of materials. Suitable materials include, but are not limited to, cellulosic materials (e.g., pulp fibers), vinyl polymers, including polyethylene, polypropylene, polybutadiene, polyisobutylene, polystyrene, polyvinylchloride, polyvinylacetate, polyvinylalcohol, polyurethane, and polyacetonitrile, synthetic rubber, polysiloxanes, terephthalate hydrocarbon polymers, such as natural rubber, polyolefines, polyesters, polyamides, polyanhidrides, fluoropolymers, nylons or any combination of the foregoing. Any material commonly used in the art may be used. In one embodiment, the material is hydrophilic. The material may be naturally hydrophilic or may be treated to become hydrophilic (such as adding an agent during or after processing). In a particular embodiment, at least one layer of the upper portion 12 is comprises polypropylene, such as polypropylene fibers alone or in combination with cellulosic materials. The polypropylene may be a spunbonded fabric of hydrophilic polypropylene fibers. The upper portion 12 may be sterile or non-sterile depending on the use of the anti-infective protector. Furthermore, the material comprising the upper portion 12 should be non-toxic to the patient.

The upper portion 12, regardless of the number of layers, may have a thickness that varies depending on the use of the anti-infective protector. In one embodiment, the upper layer 12 has a thickness from 10 to 3000 µM. In alternate embodiments, the thickness is less than 1500 µM, less than 1000 µM, less than 500 µM or less than 100 µM.

In one embodiment, the upper portion 12 further comprises at least one anti-infective agent. The anti-infective agent may be applied to the upper portion 12 after the anti-infective protector is manufactured or may be incorporated into the upper portion 12 during manufacture of the anti-infective protector. In one embodiment, the upper portion 12 may be designed to provide controlled release of the anti-infective agent. In any event, at least a portion of the anti-infective agent on the upper portion 12 is transferred from the anti-infective protector to the equipment and/or the patient during use in an amount effective to prevent or inhibit colonization of the equipment and/or patient by infective agents or is present in an amount effective to prevent colonization of the upper portion 12 by an infective agent. In one embodiment, the amount effective to prevent or inhibit colonization is an amount that is cytostatic or cytotoxic to the infective agent. As a result, the anti-infective agent thereby reduces the number and/or viability of infective agents present and thereby inhibits or prevents colonization of equipment, the patient and/or the anti-infective protector. The benefits of such outcomes are described herein.

Lower Portion

The lower portion 14 is a liquid impervious layer. The lower portion 14 prevents any liquids that enter through the liquid permeable layer 12 from exiting the anti-infective protector 10. The lower portion 14 may comprise one layer of liquid impervious material or more than one layer of liquid impervious material. In the case where the lower portion 14 comprises more than one layer of liquid impervious material, such layers may be positioned adjacent to and/or bonded to one another.

The lower portion 14 or any of the layers comprising the lower portion 14 may comprise any polymeric material. In one embodiment, the polymeric material is a film-forming polymeric material. Suitable film-forming materials include, but are not limited to, vinyl polymers, including polyethylene, polypropylene, polybutadiene, polyisobutylene, polystyrene, polyvinylchloride, polyvinylacetate, polyvinylalcohol, polyurethane, and polyacetonitrile, synthetic rubber, polysiloxanes, terephthalate hydrocarbon polymers, such as natural rubber, polyolefines, polyesters, polyamides, polyanhidrides, fluoropolymers, nylons or any combination of the foregoing.

Furthermore, such material may be selected to exhibit slip-resistance or grip, such that the anti-infective protector does not slip or fall from a piece of equipment with which it is used. Slip resistance may be defined as any material having a coefficient of friction of 0.2 or higher as measured by ASTM D1894. Such polymers that exhibit slip resistance include, but are not limited to, polyethylene. In those embodiments where the lower portion 14 comprises more than one layer, only the outermost layer (i.e., the second exposed surface 14A) may be selected to have skip resistance. Furthermore, the material comprising the second exposed surface 14A may be imprinted with a gripping pattern (such as, but not limited to, dimples, ridges, geometric patters, channels and the like) to provide additional slip resistance.

The lower portion 14, regardless of the number of layers, may have a thickness that varies depending on the use of the anti-infective protector. In one embodiment, the lower portion 14 has a thickness from 10 to 1000 μM. In alternate embodiments, the thickness is less than 500 μM, less than 250 μM, less than 100 μM, less than 50 μM or less than 10 μM.

The lower portion 14 may be joined or bonded to at least a portion of the upper portion 12. In one embodiment, the lower portion 14 and the upper portion 12 are joined or bonded along their entire periphery. In alternate embodiments, the lower portion 14 is joined or bonded to the upper portion 12 along one or more edges. In such embodiments, at least a portion of the first interior surface 12B and second interior surface 14B are in contact with one another.

In one embodiment, the lower portion 14 further comprises at least one anti-infective agent. The anti-infective agent may be applied to the lower portion 14 after the anti-infective protector is manufactured or may be incorporated into the lower portion 14 during manufacture of the anti-infective protector. In one embodiment, the lower portion 14 may be designed to provide controlled release of the anti-infective agent as described herein. In any event, at least a portion of the anti-infective agent on the lower portion 14 is transferred from the anti-infective protector to the equipment and/or the patient during use in an amount effective to prevent or inhibit colonization of the equipment and/or patient by infective agents or is present in an amount effective to prevent colonization of the lower portion 14 by an infective agent. In one embodiment, the amount effective to prevent or inhibit colonization is an amount that is cytostatic or cytotoxic to the infective agent. As a result, the anti-infective agent thereby reduces the number and/or viability of infective agents present and thereby inhibits or prevents colonization of equipment, the patient and/or the anti-infective protector. The benefits of such outcomes are described herein.

Absorbent Matrix

The anti-infective protector 10 optionally further comprises a middle portion 16 positioned between the upper portion 12 and the lower portion 14. The middle portion 16 comprises an absorbent matrix to absorb and retain at least a portion of the fluids that pass through the fluid permeable upper portion 12. In one embodiment, substantially all the fluid that passes through the liquid permeable upper portion 12 is absorbed and retained by the middle portion 16.

The middle portion 16 extends between at least a portion of the upper 12 and lower 14 portions and at least a part of the middle portion 16 is in contact with the first interior surface 12B and the second interior surface 14B. The middle portion 16 may extend between a small portion of the overall surface area defined by the upper 12 and lower 14 portions or may extend over the entire surface area defined by the upper 12 and lower 14 portions. For example, the anti-infective protector may comprise 3 layers: (i) the upper portion 12; (ii) the lower portion 14; and (iii) a middle layer 16 that is positioned in the central portion of the anti-infective protector. In such an example, the peripheral areas of the anti-infective protector may lack a middle layer 16. In another example, the anti-infective protector may comprise 3 layers: (i) the upper portion 12; (ii) the lower portion 14; and (iii) a middle layer 16 that is positioned to cover essentially all the surface area between the upper 12 and lower 14 portions. Furthermore, the middle portion 16 may be positioned in desired locations to provide the liquid absorbing and retaining function.

The middle portion 16 may be bonded to at least a portion of the upper 12 and/or lower 14 portions or may be placed between such upper 12 and lower 14 portions. Furthermore, the upper 12 and lower 14 portions may be joined or bonded to one another along at least a portion of their periphery, thereby enclosing, at least partially, the middle portion 16. In one embodiment, the middle portion 16 is enclosed completely by the upper 12 and lower 14 portions.

In one embodiment, shown in FIG. 2, the anti-infective protector 10 contains a middle portion 16 between the upper portion 12 and the lower portion 14. This middle portion 16 is designed to absorb bodily fluids and distribute and/or retain those fluids within and throughout the middle portion 16. The absorbent layer may be sufficiently soft and flexible so as to comfortably conform to surfaces of the equipment and/or patient to provide increased comfort and close fit.

In one embodiment, the absorbent matrix of the middle portion 16 may comprise a superabsorbent polymer (SAP). SAPs are polymers that can absorb and retain large amounts of a liquid relative to their own mass. Liquid absorbing polymers, classified as hydrogels, absorb aqueous solutions through hydrogen bonding with the liquid molecules, such as water molecule. In some cases, a SAP may absorb 500 times its weight. SAPs are commonly made from the polymerization of acrylic acid blended with sodium hydroxide in the presence of an initiator to form a poly-acrylic acid, sodium salt (sometimes referred to as cross-linked sodium polyacrylate). Other materials are also used to make a SAPs, such as, but not limited to, polyacrylamide copolymer, ethylene maleic anhydride copolymer, cross-linked carboxymethyl-cellulose, polyvinyl alcohol copolymers, cross-linked polyethylene oxide, and starch grafted copolymer of polyacrylonitrile. The total absorbency and swelling capacity are controlled by the type and degree of cross-linking to the polymer. Low density cross-linked SAP generally has a higher absorbent capacity and swells to a larger degree. These types of SAPs also have a softer and more cohesive gel formation. High cross-link density polymers exhibit lower absorbent capacity and swell. The gel strength is firmer and can maintain particle shape even under modest pressure. The present disclosure is mean to encompass any SAP for use therein. Such absorbent materials are well known in the art (see U.S. Pat. Nos. 5,866,242, 5,916,670 and 6,485,667).

The middle portion 16 may comprise other layers in addition to the absorbent matrix. For example, the middle portion 16 may comprise a SAP in combination with a cellulosic material (e.g., pulp fibers) or any other material from which the upper portion 12 is formed. In one embodiment, the middle portion 16 comprises a SAP sandwiched between to layers of cellulosic materials (e.g., pulp fibers) or other materials.

The middle portion 16, regardless of the number of layers, may have a thickness that varies depending on the use of the anti-infective protector. In one embodiment, the middle portion 16 has a thickness from 10 to 3000 μM. In alternate embodiments, the thickness is less than 2000 ∞M, less than 1000 μM, less than 500 μM, less than 250 μM or less than 100 μM. The thicknesses described above are measured before exposure to liquid.

In one embodiment, the middle portion 16 further comprises at least one anti-infective agent. The anti-infective agent may be mixed within the middle portion 16 or may be applied to a layer surrounding the middle portion 16. In one embodiment, the middle portion 16 may be designed to provide controlled release of the anti-infective agent as described herein. In any event, at least a portion of the anti-infective agent on the middle portion 16 is transferred from the anti-infective protector to the liquid coming into contact with the middle portion 16 in an amount effective to prevent or inhibit colonization of the equipment and/or patient by infective agents or is present in an amount effective to prevent colonization of the upper 12 or lower portion 14 by an infective agent. In one embodiment, the amount effective to prevent or inhibit colonization is an amount that is cytostatic or cytotoxic to the infective agent. As a result, the anti-infective agent thereby reduces the number and/or viability of infective agents present and thereby inhibits or prevents colonization of equipment, the patient and/or the anti-infective protector. The benefits of such outcomes are described herein.

Anti-Infective Agents

In those embodiments where one or more of the upper 12, middle 16 or lower 14 portions or layer 30 (described below) comprises an anti-infective agent, the anti-infective agent may be applied to the surface of, dispersed within or incorporated into the material comprising the upper 12, middle 16 or lower 14 portion or layer 30. The anti-infective agent may be applied to or incorporated into the appropriate portion by blowing, coating, spraying, immersion, dry blending, melt incorporation or any other method know in the art.

In those embodiments where more than one of the upper 12, lower 14 and middle 16 portions contain an anti-infective agent, the nature of the anti-infective agents in each layer may be the same or may be different. For instance, the anti-infective agent on the upper portion 12 may be an antimicrobial agent and an antiviral agent, while the anti-infective agent in the middle portion 16 may be solely an antimicrobial agent. Furthermore, the different layers may contain anti-infective agents based on the type of infective agent to be encountered in the healthcare setting. The concentrations of the anti-infective agents may also differ between layers. Therefore, an anti-infective protector of the present disclosure designed for use in a healthcare setting may have a different combination of anti-infective agents (which may contain, for example, anti-infective agents designed to combat bacterial pathogens, such as but not limited to MRSA) than an anti-infective protector designed for use in a doctor's office (which may contain, for example, anti-infective agents designed to combat viral pathogens, such as but not limited to, the cold or flu virus). Each portion or when multiple layers are present in a portion, each layer, may contain one or more anti-infective agents.

In one embodiment, the upper 12, lower 14 and middle 16 portions contain from about 0.001% to about 10% (by weight) of anti-infective agent when such anti-infective agent is present. In an alternate embodiment, from about 0.01% to about 5% (by weight), or from about 0.01% to about 2% (by weight) or from about 0.1% to about 1% (by weight) In any case, the anti-infective agent is present in an effective amount.

The anti-infective agent may be a cytostatic or a cytotoxic agent. The anti-infective agent may be an antibiotic, an alcohol (including, but not limited to, ethanol and isopropanol) an aldehyde (including, but not limited to, glutaraldehyde and formaldehyde), a halogen-releasing compound (including, but not limited to, chlorine compounds and iodine compounds), a peroxide (including, but not limited to, hydrogen peroxide, ozone and peracetic acid), an anilide (including, but not limited to, triclocarban), a biguanide (including, but not limited to, chlorhexidine, alexidine and polymeric biguanides), a bisphenols (including, but not limited to, triclosan hexachlorophene), a halophenol (including, but not limited to, PCMX (p-chloro-m-xylenol)), a heavy metal/noble metal-ion (including, but not limited to, silver compounds and mercury compounds), a phenol or cresol, a quaternary ammonium compound (including, but not limited to, cetrimide, benzalkonium chloride and cetylpyridinium chloride).

In one embodiment, when the anti-infective agent is an anti-bacterial agent is a noble metal-ion, such as but not limited to silver or copper, triclosan, triclosan SDC (triclosan silver dihydrogen citrate) amoxicillin, aminoglycosides, beta-lactam (glycopeptide), betalactamases, clindamycin, chloramphenicol, cephalosporins, ciprofloxacin, erythromycin, fluroquinolones, macrolides, metronidazole, penicillins, quinolones, ritampin, streptomycin, sulfonamide, tetracyclines, trimethoprim, trimethoprim-sulfamthoxazole, vancomycin and combinations of the foregoing.

In a specific embodiment, the anti-infective agent is a noble metal-ion, such as silver. Such noble metal ions are known for their antimicrobial properties and have been used in medical care for many years to prevent and treat infection. In recent years, this technology has been applied to consumer products to prevent the transmission of infectious disease and to kill harmful bacteria such as *S. aureus* and *Salmonella*. In common practice, noble metals, metal-ions, metal salts or compounds containing metal-ions having antimicrobial properties, and other antimicrobial materials such as isothiazolone and chlorophenyl compounds (such as Triclosan, also known as 5-chloro-2-(2,4-dichlorophenoxy) phenol), can be applied to surfaces to impart an antimicrobial property to the surface. If, or when, the surface is inoculated with infective agents, the noble metals, metal-ions, metal complexes or compounds containing any of the foregoing will slow or prevent the growth and/or reproduction of infective agents. Metallic ions function by entering the bacterial cells and reacting with polypeptides and other anions (negative charged species), rendering the polypeptides insoluble and thereby inactive. Inactive polypeptides perturb cellular function, disrupt membranes and prevent the normal activity and reproduction. Silver ion ($Ag^+$ or $Ag^{2+}$) is perhaps the best known metal ion antimicrobial due to its unusually good bioactivity at low concentrations. This bioactivity of silver is known as oligodynamic action.

In a specific embodiment, the anti-infective agent is triclosan (5-chloro-2-(2,4-dichlorophenoxy)phenol). Triclosan binds to bacterial enoyl-acyl carrier protein reductase enzyme which is encoded by the gene FabI. This binding increases the enzyme's affinity for nicotinamide adenine dinucleotide ($NAD^+$). This results in the formation of a stable ternary complex of ENR-$NAD^+$-5-chloro-2-(2,4-dichlorophenoxy)phenol, which is unable to participate in fatty acid synthesis. Fatty acid is necessary for reproducing and building cell membranes. Humans do not have an ENR enzyme, and thus are not affected.

In another specific embodiment, the anti-infective agent is 2-propanol (available under the trade name Microban). 2-propanol has been demonstrated to be effective against a number of infective agents, including gram-positive and gram-negative bacteria, ammonia-producing bacteria, fungi, dermatophytes, resident skin bacteria, molds, and yeasts. 2-propanol acts as a cell wall rupturing agent. 2-propanol has been demonstrated as safe against human cells (due to a more complex cell wall structure) and is safely eliminated from the human body after consumption. As discussed above, 2-propanol may be introduced into the various portions of the anti-infective protector during manufacture or applied once the anti-infective protector is manufactured.

In a further embodiment, the anti-infective protector may be designed to provide controlled release of the anti-infective agent. The nature of the particular compound used for time release may depend on the nature of the use of the anti-infective protector, the nature of the anti-infective agent and/or the portion or layer to which the anti-infective agent is applied. Such controlled release may be triggered by exposure to liquid, pH change, temperature change, exposure to light, wear of the layer into which the anti-infective agents is incorporated and other triggering mechanisms known in the art.

One class of polymers that are suitable for use in the present disclosure is hydrogels. Hydrogels exist in two state: (i) a first state wherein the hydrogel is in a compact state; and (ii) a second state wherein the hydrogel is in an expanded state. In the second state, the hydrogel may release agents, such as an anti-infective agent, that are trapped within the hydrogel in the first state. The hydrogel does not dissolve when in the second state. The hydrogel may be triggered to switch from the first state to the second state by a variety of factors, such as exposure to a liquid, a change in pH, a change in temperature, exposure to light or any of several other factors. The triggering criteria for transition between the first and second states may vary depending on the particular polymer used to manufacture the hydrogel. One example of a pH-triggered hydrogel is poly[methacrylic acid-g-poly(ethylene glycol)]. An example of a temperature-triggered hydrogel is poly(N-isopropylacrylamide).

Based on the level of cross-linking present in the chosen polymer, release rates can be tailored to meet specific needs. Additionally, many hydrogels, such as those containing polyacrylic acid backbones, are classified as SAPs and can contain over 99% water. Therefore, in one embodiment, the same material that forms the middle portion 16 of the anti-infective protector 10 is also used for the controlled release of the anti-infective agent. In addition to the pH-triggered hydrogel listed above, poly(ethylene glycol), or PEG, based polyurethanes are also appropriate. For these PEG-based polyurethanes, the hydrogels can swell to over 1000% of their original size when introduced into a liquid environment.

Other polymers considered for use in controlled release applications because of their properties include, but are not limited to, poly(2-hydroxy ethyl methacrylate), poly(N-vinyl pyrrolidone), poly(methyl methacrylate), poly(vinyl alcohol), polyacrylamide, poly(ethylene-co-vinyl acetate), poly(methacrylic acid), polylactides (PLA), polyglycolides (PGA), poly(lactide-co-glycolides) (PLGA), polyanhydrides and polyorthoesters.

Thermoresponsive polymers are macromolecules which undergo a physical change when exposed to changing temperature. The temperature sensitive property of these polymers usually correlates with the existence of a lower critical solution temperature (LCST) below which the polymer becomes insoluble in water. The most commonly used thermoresponsive polymer is Poly(N-isopropylacrylamide), also known as PNIPAM, NiPAAm, or poly-NiPAAm. NiPAAm exhibits an LCST at 32° C., meaning that the solution of NiPAAm and water gels at ~90° F., at which time the polymer would release the active agent encapsulated therein. NiPAAm can also be tailored to gel closer to 99° F. by forming a copolymer of NiPAAm and acrylic acid (poly(N-isopropylacrylamide-co-acrylic acid or NiPAAm/ AAc). The LCST of the copolymer is higher than that of NiPAAm because of the added interactions of the hydrophilic co-monomer (acrylic acid) with water. At any temperature below the LCST, the polymer is stable and the active agent remains encapsulated therein.

Others in this family include: poly(N,N'-diethylacrylamide), poly(N-ethyl,N-methylacrylamide) and poly(N-pyrrolidinoacrylamide). There are numerous variations of each of the above-mentioned polymers. Different embodiments of the same polymer can vary based on the degree of cross-linking, molecular weight, and method of polymerization, among other things. Another example of a thermoresponsive polymer that is not a member of the above-mentioned family is poly(vinylmethyl ether). Thermoresponsive polymers have also been produced from biodegradable poly(amino acids).

Photoresponsive polymers undergo physical changes when exposed to light, whether it be UV or visible. Generally, these polymers undergo phase separation when exposed to ultraviolet light, as in the case of Poly(N-isopropylacrylamide) with pendant azobenzene chromophores. Another example of a photoresponsive polymer is polyacrylamide having triphenylmethane leucocyanide groups. For the latter polymer, photodissociation caused by ultraviolet irradiation expanded the gel up to 18 times its original volume. This expansion would allow an anti-infective agent encapsulated within the polymer to be released into the solution. Additional examples of photoresponsive polymers include a vinyl copolymer carrying crown ether and spirobenzopyran side chains and a polyelectrolyte of polyacrylic acid with spiropyran in the side chain.

Single Layer Anti-Infective Protectors

Figure 3:
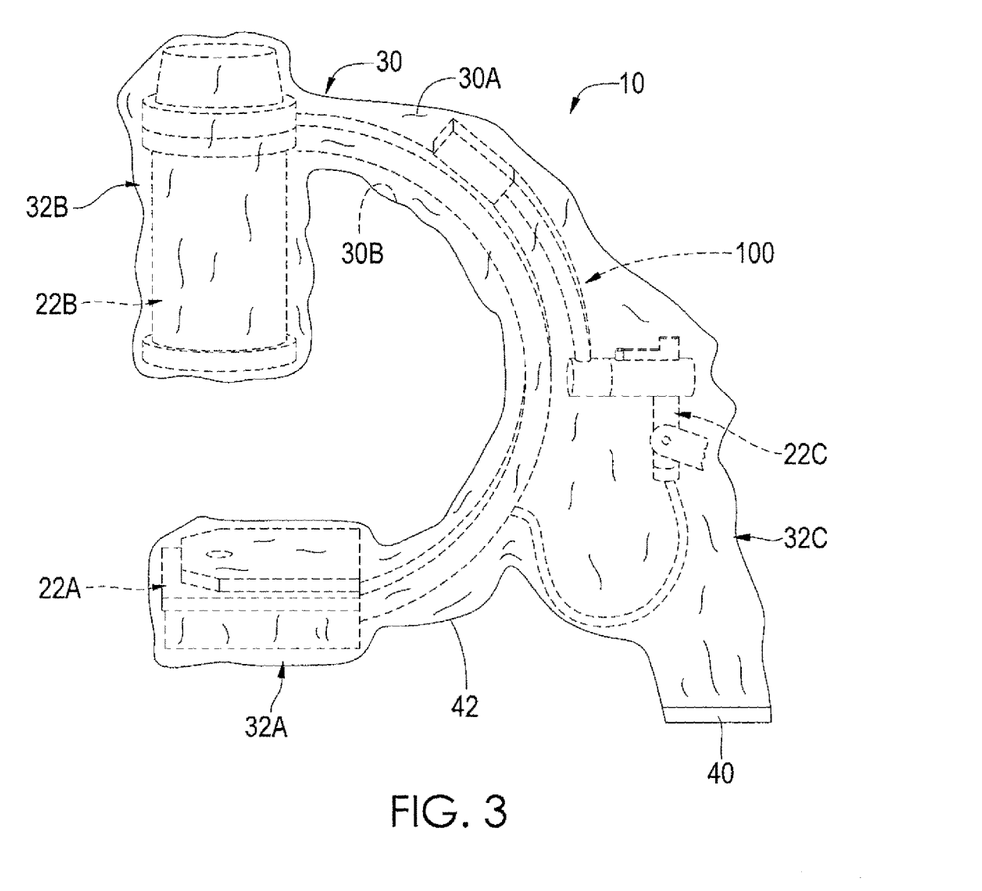
FIG. 3 shows a prospective view of one embodiment of an anti-infective protector of the present disclosure configured to receive a C-arm.
Figure 4:
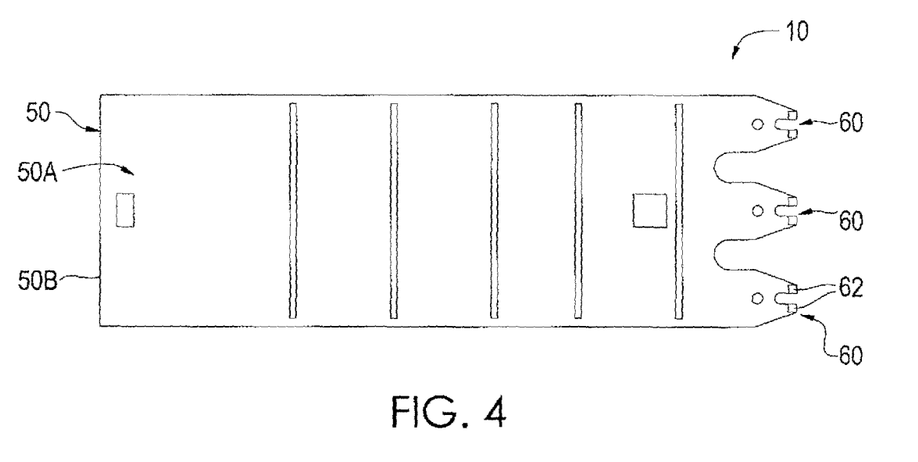
FIG. 4 shows a prospective view one embodiment of an anti-infective protector of the present disclosure configured to receive a surgical microscope.

In another embodiment, the anti-infective protector comprises a single layer of material. Examples of this embodiment are illustrated in FIGS. 3 and 4 (although the anti-infective protector may be designed for other equipment in the healthcare setting as well).

In such an embodiment, the anti-infective protector comprises a single layer of material 30 having a first exposed surface 30A and a second exposed surface 30B. In such anti-infective protectors, one of the first or second exposed surfaces is exposed to the ambient environment and the other of the first or second exposed surfaces is exposed to and contacts at least a portion of the equipment to which it is applied.

The material 30 is manufactured from a liquid impervious material. The liquid impervious material creates a barrier around the equipment being protected with the benefits described herein. The material 30 may be manufactured from any polymeric material. In one embodiment, the polymeric material is a film-forming polymeric material. Suitable film-forming materials include, but are not limited to, vinyl polymers, including polyethylene, polypropylene, polybutadiene, polyisobutylene, polystyrene, polyvinylchloride, polyvinylacetate, polyvinylalcohol, polyurethane, and polyacetonitrile, synthetic rubber, polysiloxanes, terephthalate hydrocarbon polymers, such as natural rubber, polyolefines, polyesters, polyamides, polyanhidrides, fluoropolymers, nylons or any combination of the foregoing.

Furthermore, the material may be selected to exhibit slip-resistance or grip, such that the anti-infective protector does not slip or fall from a piece of equipment with which it is used. Slip resistance may be defined as any material having a coefficient of friction of 0.2 or higher as measured by ASTM D1894. Such polymers that exhibit slip resistance include, but are not limited to, polyethylene. Furthermore, at least one of the first exposed surface 30A and a second exposed surface 30B may be imprinted with a gripping pattern (such as, but not limited to, dimples, ridges, geometric patters, channels and the like) to provide additional slip resistance.

The material 30 may have a thickness that varies depending on the use of the anti-infective protector. In one embodiment, the material 30 has a thickness from 10 to 1000 μM. In alternate embodiments, the thickness is less than 500 μM, less than 250 μM, less than 100 μM, less than 50 μM or less than 10 μM.

In one embodiment, the material 30 further comprises at least one anti-infective agent. Suitable anti-infective agents are described above. The anti-infective agent may be applied to at least one of the first exposed surface 30A and a second exposed surface 30B after the anti-infective protector is manufactured or may be incorporated into the material 30 during manufacture of the anti-infective protector as described herein. In one embodiment, material 30 may be designed to provide controlled release of the anti-infective agent as described herein. In any event, at least a portion of the anti-infective agent on the material 30 is transferred from the anti-infective protector to the equipment during use in an amount effective to prevent or inhibit colonization of the equipment by infective agents or is present in an amount effective to prevent colonization of the anti-infective cover by an infective agent. In one embodiment, the amount effective to prevent or inhibit colonization is an amount that is cytostatic or cytotoxic to the infective agent. As a result, the anti-infective agent thereby reduces the number and/or viability of infective agents present and thereby inhibits or prevents colonization of equipment. The benefits of such outcomes are described herein.

Additional Features

The multi-layer and single layer anti-infective protectors described herein may also comprise other features that improve operability. In one embodiment, the anti-infective protector may comprise one or more clear or transparent areas to allow for viewing the controls, position or readout of a particular piece of equipment. In certain embodiments, the entirety of the material comprising the anti-infective protector is clear/transparent. Therefore, in one embodiment, the anti-infective protector provides the benefits described herein without interfering with the use of the equipment to which it is applied. The nature, dimensions and location of such clear/transparent areas may be determined based on the particular piece of equipment or the use of the anti-infective protector.

In a further embodiment, the anti-infective protector may comprise a fitting element on at least a portion thereof. The fitting element may be any element that allows the anti-infective protector to follow the contours of the equipment to which it is applied. In one embodiment, the fitting element is cuff portion. The cuff portion may comprise an elastic portion if desired. For example, in an anti-infective protector designed for use with a flat surface (such as, but not limited to, a patient table or examination table), the anti-infective protector may comprise an elastic cuff that extends along at least a portion of the periphery of the anti-infective protector. The cuff portion allows a user to quickly place the anti-infective protector on the equipment. Furthermore, if an elastic element is included in the cuff portion, the anti-infective protector is held snugly in place on the equipment.

In an alternate embodiment, fitting element may be a pocket formed in a desired portion of the anti-infective protector or a specifically contoured portion. For example, in an anti-infective protector designed for use with a surgical microscope, the anti-infective protector may comprise a pocket or a specifically contoured portion to receive the ocular portions of the microscope. As discussed above, a portion of the pocket may be equipped with a clear/transparent portion to allow for viewing through the ocular portion. The pocket/contoured portion allows a user to quickly place the anti-infective protector on the equipment and aids in the proper placement of the anti-infective protector The embodiments described above may be combined as is known in the art.

The fitting elements may be positioned along and be of sufficient dimensions as dictated by the piece of equipment with which the anti-infective protector is used. The fitting elements may be joined to any portion of the anti-infective protector. The fitting element may be formed of any material described herein; however, in one embodiment, the fitting element is formed of the same material as the portion to which it is attached. In an alternate embodiment, the fitting element may be formed of any material known in the art for such purposes.

In still a further embodiment, the anti-infective protector may comprise specifically configured areas or pockets to receive a piece of equipment or portion thereof. In such embodiment, all layers or portions may comprise the configured areas or pockets. The nature of the specifically configured areas or pockets may be configured to conform to the equipment to which the anti-infective protector is applied.

In yet another embodiment, the anti-infective protectors described herein may be disposable or may be reusable. Furthermore, the anti-infective protectors may be provided initially as sterile articles or non-sterile articles depending on their intended use.

Methods of Using

The present disclosure provides for methods of using the anti-infective protector. In one embodiment, such methods comprise providing an anti-infective protector of the present disclosure and placing a second exposed surface of the anti-infective protector in contact with at least a portion of a piece of equipment in the healthcare setting and a first exposed surface of the anti-infective protector in contact with at least a portion of a patient or the ambient surrounding of the healthcare setting. For example, in a surgical setting, the anti-infective protector may be placed between the patient and the patient table thereby covering and contacting at least a portion of the patient table and contacting at least a portion of the patient. The anti-infective protector serves as an active barrier preventing the transfer of infective agents from the patient and others in the healthcare setting to equipment in the healthcare setting and, in the case where infective agents are present on equipment, from the to the patient and others present in the healthcare setting. As a result, the colonization by infective agents of equipment, patients and others in the healthcare setting is prevented or reduced, thereby reducing or preventing the contraction and/or spread of nosocomial and other infections.

In operation, the second exposed surface contacts the piece of equipment and/or surface being protected while the first exposed surface the patient or is exposed to the environment. The anti-infective agents contained in the first and/or second exposed surfaces are released (either through a controlled release or other mechanism) and contacts the equipment and/or patient and prevents or reduces the transmission of infective agents from the patient/others to the equipment and vice-versa, with the benefits described herein. Furthermore, the anti-infective agent in the first and/or second exposed surfaces prevents colonization of the anti-infective protector from the infective agents present in the environment or equipment, respectively.

In the embodiment where the anti-infective protector comprises an absorbent middle portion, the middle portion functions to absorb liquids, such as but not limited to, bodily fluids released from the patient or the procedure. The middle portion may further comprise an anti-infective agent to control the spread of any infective agents present in such bodily fluid. Therefore, any bodily fluid released in absorbed by the middle portion are exposed to anti-infective agents (if present) in the middle portion. As a result, the colonization by infective agents of equipment, patients and others in the healthcare setting is prevented or reduced, thereby reducing or preventing the contraction and/or spread of nosocomial and other infections.

The anti-infective protector of the present disclosure may be designed for use with a particular piece of equipment. The dimensions, material, nature of infective agent and other characteristics of the anti-infective protector may be selected based on the piece of equipment with which it will be used, the setting in which the equipment is used and the nature of the use, among other factors.

As discussed herein, the anti-infective protector may be used with any equipment used in a healthcare setting. Exemplary items of equipment include, but are not limited to, equipment that is used at a patient's bedside, equipment used for patient diagnosis and equipment that used during surgery; as is known, some items of equipment may be used in both settings.

Specific items of equipment include, but are not limited to, IV infusion pumps, pain pumps, DVT compression pumps, pulse oxymeter monitors, respiratory ventilators, respiratory therapy machines, portable EKG machines, negative pressure wound drainage pumps, portable x-ray machines, x-ray machines, ultrasound machines, computer-assisted tomography machines, radiation delivery devices, surgical microscopes, portable liquid waste suction machines, portable C-arm machines, fluid warming machines, patient warming machines, slush machines, surgical cameras, video equipment towers and monitors, back tables, mayo stand tables, basin stands, surgical patient tables, mattresses and accessories, kick buck sponge receptacles, blood capturing/treatment machines, cardiovascular perfusion pumps, contaminated instrument transport trays and carts, contaminated instrument transport lifts, patient transfer devices, electocutery machine, smoke evacuator machines, negative pressure wound drainage machines, lavage machines, navigation systems, vascular doppler devices, nerve stimulation machines and computer keyboards and monitors In one embodiment, the anti-infective protector 10 is designed to cover (at least partially) or receive (at least partially) a piece of medical diagnostic equipment, such as, but not limited to, a C-arm (FIG. 3). The design and use of C-arms is well known in the art; therefore, the anti-infective protector can be easily designed using the teachings of the present disclosure to accommodate such devices. The C-arm is indicated generally by the number 100 and comprises several portions: (i) a central C-arm supported by a stand, 22C; (ii) a top portion, 22B; and (iii) a bottom portion 22A. The anti-infective protector is designated generally as 10 and covers at least a portion of the C-arm 100. The anti-infective protector 10 is illustrated as comprising a single surface 30, the singe surface 30 having a first exposed surface 30A exposed to the ambient environment and second exposed surface 30B contacting at least a portion of the C-arm 100. Although not illustrated in FIG. 3, the anti-infective protector may further comprise other layers, such as a middle portion and a bottom portion (as described herein) The anti-infective protector further comprises pockets 32A, 32B and 32C to receive elements 22A, 22B and 22C, respectively. The pockets are designed in the anti-infective protector to aid in securing the anti-infective protector to the C-arm 100 as discussed herein. Furthermore, the anti-infective protector may comprise a securing element, illustrated herein as cuff 40 or contoured portion 42 to secure the anti-infective protector to a portion 22C of the C-arm 100. As discussed herein, the general configuration of the anti-infective protector 10 may be varied depending on the nature of the C-arm 100.

In an alternate embodiment, the anti-infective protector 10 is designed to cover (at least partially) or receive (at least partially) a piece of medical diagnostic equipment, such as, but not limited to, a surgical microscope (FIG. 4). The design and use of surgical microscopes is well known in the art; therefore, the anti-infective protector can be easily designed using the teachings of the present disclosure to accommodate such devices. FIG. 4 shows an exemplary anti-infective protector for a surgical microscope. The anti-infective protector is designated generally as 10 and comprises a singe surface 50 with a first exposed surface 50A and a second exposed surface 50B. Although not illustrated in FIG. 4, the anti-infective protector may further comprise other layers, such as a middle portion and a bottom portion (as described herein). The anti-infective protector 10 further comprises pocket portions 60 to receive the ocular portions of the surgical microscope. The pocket portions 60 may further comprise a clear/transparent portion 62. As discussed herein, the general configuration of the anti-infective protector 10 may be varied depending on the nature of the C-arm 100.

In alternate embodiments, the anti-infective protector 10 is designed to cover (at least partially) or receive (at least partially) a mattress, support or other surface on a patient table. In this embodiment, the anti-infective protector 10 keeps any bodily fluids which may contain infective agents from contacting equipment or surface in the healthcare setting, with the benefits as described herein.

In still a further embodiment, the anti-infective protector 10 is provided as a part of what is commonly known in the art as an operating room (OR) or patient room turnover kit designed to aid health care providers in quickly, safely and cheaply remove all contaminated linens and other materials from an OR and rapidly prepare the OR for the next patient.

While the invention has been described with respect to a limited number of embodiments, those skilled in the art, having benefit of this disclosure, will appreciate that other embodiments can be devised which do not depart from the scope of the invention as disclosed here.

What is claimed:
1. A multilayer anti-infective protector comprising:
a. an anti-infective agent;
b. a liquid permeable upper portion having a first exposed surface and a first interior surface; and
c. a liquid impervious lower portion having a second exposed surface and a second interior surface, the liquid impervious lower portion adapted to contact a surface to be protected at the second exposed surface;
wherein the anti-infective agent is at least one of a noble metal-ion, chlorhexidine, triclosan or 2-propanol incorporated into and present only in the lower portion, and the lower portion is adapted for a controlled release of the anti-infective agent from an exposure to liquid, a pH change, a temperature change, or an exposure to light, wherein the controlled release is at least one of a sustained release, a slow release, a prolonged release, or a combination thereof.

2. The anti-infective protector of claim 1, wherein the anti-infective agent is at least one of a cytostatic agent or a cytotoxic agent.

3. The anti-infective protector of claim 1, wherein the anti-infective agent is present in an amount effective to prevent colonization by an infective agent.

4. The anti-infective protector of claim 1, wherein at least one of the upper portion or the lower portion contains more than one layer.

5. The anti-infective protector of claim 1, further comprising a fluid absorbing middle portion.

6. The anti-infective protector of claim 5, wherein the middle portion comprises at least one of a super absorbent polymer or a hydrogel.

7. The anti-infective protector of claim 1, wherein the lower portion is manufactured from polyethylene.

\* \* \* \* \*